(12) United States Patent
Domingues et al.

(10) Patent No.: US 10,455,923 B1
(45) Date of Patent: Oct. 29, 2019

(54) ENTERAL FEEDING SYSTEM

(71) Applicants: Heather Domingues, Matawan, NJ (US); Anthony Pezzello, Matawan, NJ (US)

(72) Inventors: Heather Domingues, Matawan, NJ (US); Anthony Pezzello, Matawan, NJ (US)

( * ) Notice: Subject to any disclaimer, the term of this patent is extended or adjusted under 35 U.S.C. 154(b) by 14 days.

(21) Appl. No.: 15/936,641

(22) Filed: Mar. 27, 2018

(51) Int. Cl.
  *A45F 3/08* (2006.01)
  *A61J 15/00* (2006.01)

(52) U.S. Cl.
  CPC ............. *A45F 3/08* (2013.01); *A61J 15/0026* (2013.01)

(58) Field of Classification Search
  CPC ........ A45F 2003/003; A45F 3/08; A45F 3/10; A61M 2005/1416; A61M 5/14244; A61M 2202/0482; A61M 2209/088; B67D 2210/00131
  See application file for complete search history.

(56) References Cited

U.S. PATENT DOCUMENTS

| | | | | |
|---|---|---|---|---|
| 3,090,621 | A * | 5/1963 | Heimers | A45F 3/14 224/200 |
| 4,438,763 | A * | 3/1984 | Zablen | A45F 3/14 128/845 |
| 4,688,595 | A | 8/1987 | Srebnik | |
| 4,796,790 | A * | 1/1989 | Hamilton | A45C 11/00 206/438 |
| 5,161,722 | A * | 11/1992 | Hembree | A45F 3/08 224/148.2 |
| 5,478,211 | A * | 12/1995 | Dominiak | A61M 5/142 417/234 |
| 5,529,220 | A * | 6/1996 | Credle, Jr. | B67D 1/04 221/96 |
| 5,700,257 | A | 12/1997 | Minick | |
| 5,799,846 | A | 9/1998 | Pfleger | |
| 6,082,589 | A * | 7/2000 | Ash | B67D 1/04 222/146.6 |
| 6,230,952 | B1 * | 5/2001 | Jupiter | A45F 3/04 150/113 |
| 6,516,981 | B2 * | 2/2003 | Perez | A41D 13/0012 2/102 |
| 6,629,955 | B2 * | 10/2003 | Morris | A61M 5/14228 604/153 |
| 6,708,991 | B1 * | 3/2004 | Ortlieb | A61M 5/1415 248/122.1 |
| 7,282,044 | B2 * | 10/2007 | Hudson | A45F 3/04 604/174 |

(Continued)

FOREIGN PATENT DOCUMENTS

CA    1272920 A    8/1990

*Primary Examiner* — Brian D Nash (57) ABSTRACT

The enteral feeding system accessory is configured for use with an enteral feeding system. The enteral feeding system comprises a feeding tube and a feeding machine. The feeding tube is a gastric catheter. The feeding machine is a pump and reservoir that pumps nutrition through the feeding tube to a patient. The enteral feeding system accessory is luggage item that is configured to transport the enteral feeding system. The enteral feeding system accessory comprises a stanchion, a plurality of mounting brackets, and a backpack. The plurality of mounting brackets attach to the stanchion. The stanchion and plurality of mounting brackets are attached to and contained within the backpack.

16 Claims, 5 Drawing Sheets

(56) References Cited

U.S. PATENT DOCUMENTS

| | | | |
|---|---|---|---|
| D622,377 S | 8/2010 | Jackson | |
| 7,832,663 B1* | 11/2010 | Cotham | A01C 7/02 |
| | | | 239/653 |
| D783,272 S | 4/2017 | Burton | |
| D791,937 S * | 7/2017 | Schoenig | D24/128 |
| 2002/0043059 A1* | 4/2002 | Konzak | A01F 12/00 |
| | | | 56/12.8 |
| 2005/0224534 A1* | 10/2005 | Hudson | A45F 3/04 |
| | | | 224/158 |
| 2008/0208116 A1* | 8/2008 | Dao | A61M 1/06 |
| | | | 604/74 |
| 2012/0150112 A1* | 6/2012 | Hershey | A61J 15/0096 |
| | | | 604/134 |
| 2013/0204074 A1* | 8/2013 | Belval | A61G 11/00 |
| | | | 600/22 |
| 2015/0265352 A1 | 9/2015 | Johnson | |
| 2016/0067148 A1* | 3/2016 | Nordquist | A61M 5/1418 |
| | | | 604/28 |
| 2016/0313104 A1* | 10/2016 | Williamson | F42B 39/02 |
| 2016/0317392 A1* | 11/2016 | Harris | A61J 15/0026 |
| 2019/0001116 A1* | 1/2019 | Jedwab | A61M 5/168 |

* cited by examiner

ENTERAL FEEDING SYSTEM

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical or veterinary science including devices for administering nutrition, more specifically, an accessory for a feeding tube for therapeutic purposes.

SUMMARY OF INVENTION

The enteral feeding system accessory is configured for use with an enteral feeding system. The enteral feeding system comprises a feeding tube and a feeding machine. The feeding tube is a gastric catheter. The feeding machine is a pump and reservoir that pumps nutrition through the feeding tube to a patient. The enteral feeding system accessory is luggage item that is configured to transport the enteral feeding system. The enteral feeding system accessory comprises a stanchion, a plurality of mounting brackets, and a backpack. The plurality of mounting brackets attach to the stanchion. The stanchion and plurality of mounting brackets are attached to and contained within the backpack.

These together with additional objects, features and advantages of the enteral feeding system accessory will be readily apparent to those of ordinary skill in the art upon reading the following detailed description of the presently preferred, but nonetheless illustrative, embodiments when taken in conjunction with the accompanying drawings.

In this respect, before explaining the current embodiments of the enteral feeding system accessory in detail, it is to be understood that the enteral feeding system accessory is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the enteral feeding system accessory.

It is therefore important that the claims be regarded as including such equivalent construction insofar as they do not depart from the spirit and scope of the enteral feeding system accessory. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
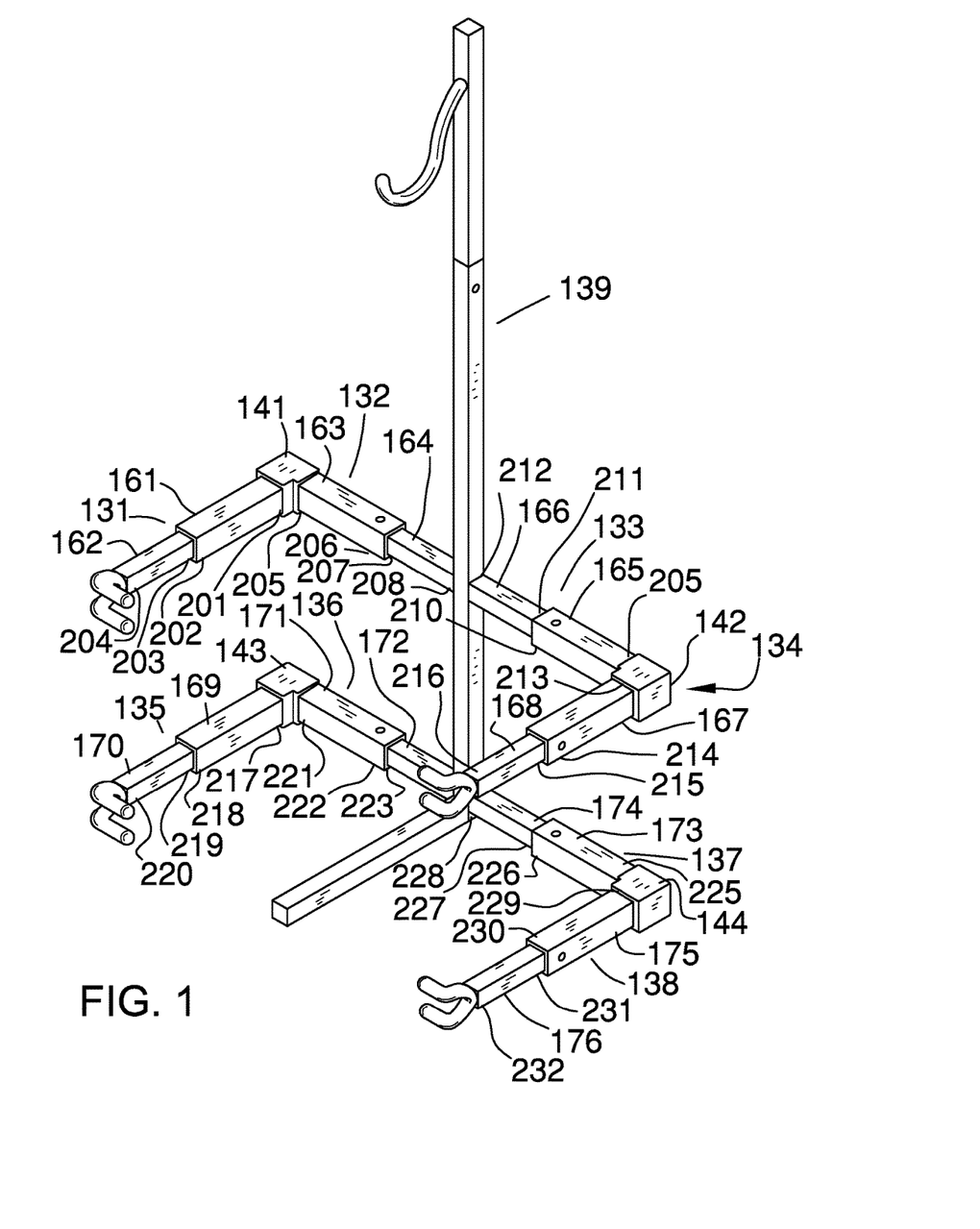
FIG. 1 is a perspective view of an embodiment of the disclosure.
Figure 2:
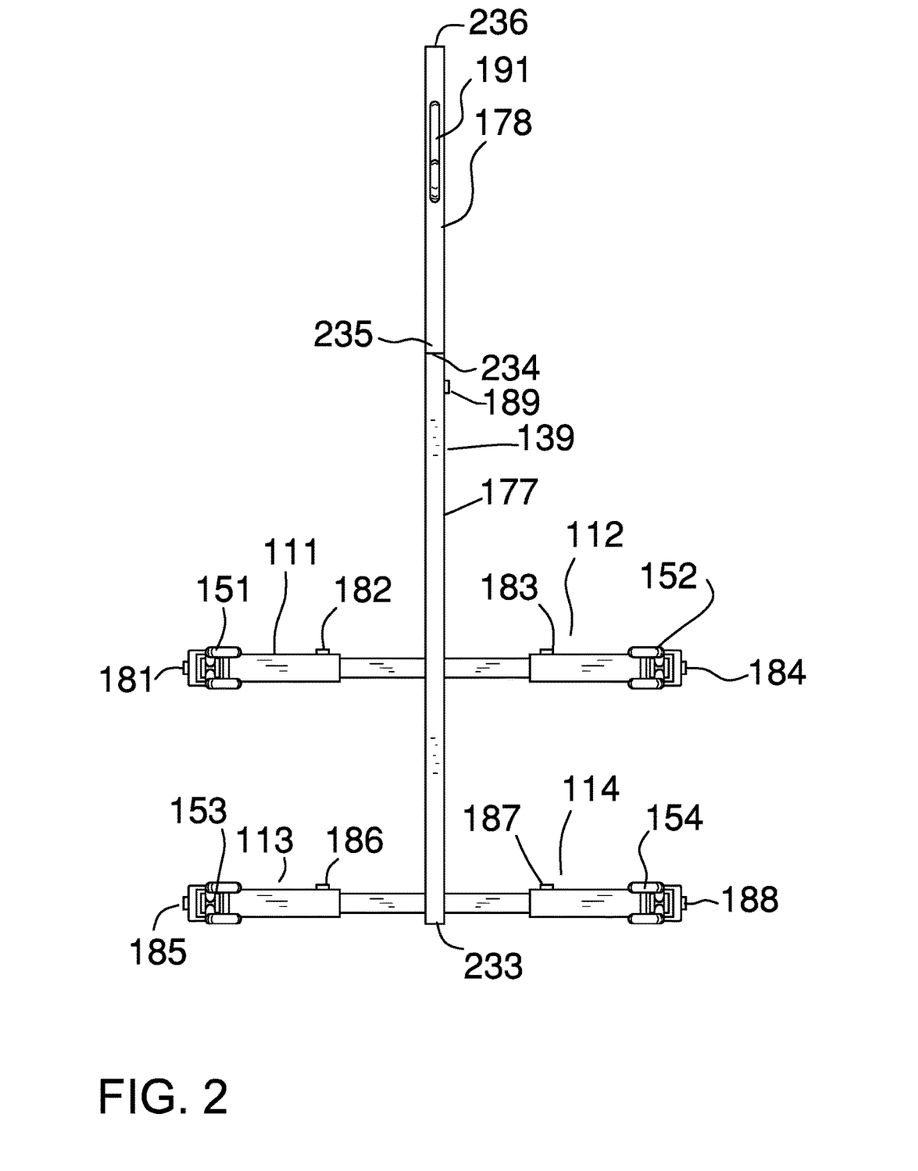
FIG. 2 is a front view of an embodiment of the disclosure.
Figure 3:
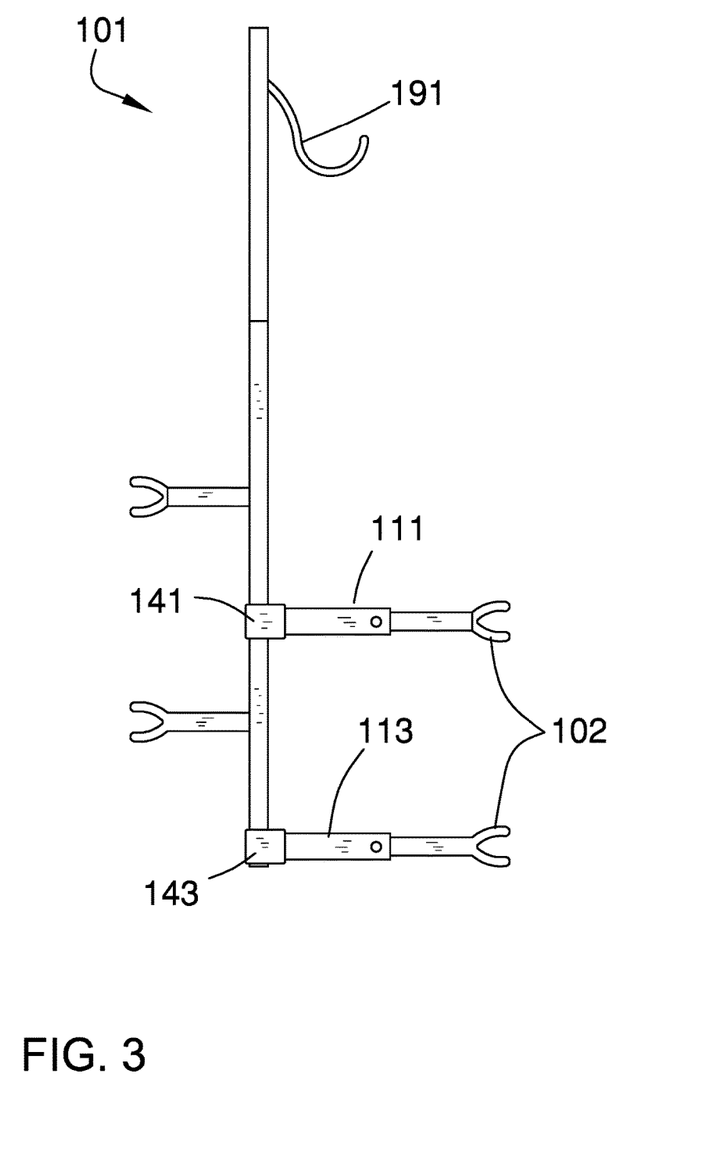
FIG. 3 is a side view of an embodiment of the disclosure.
Figure 4:
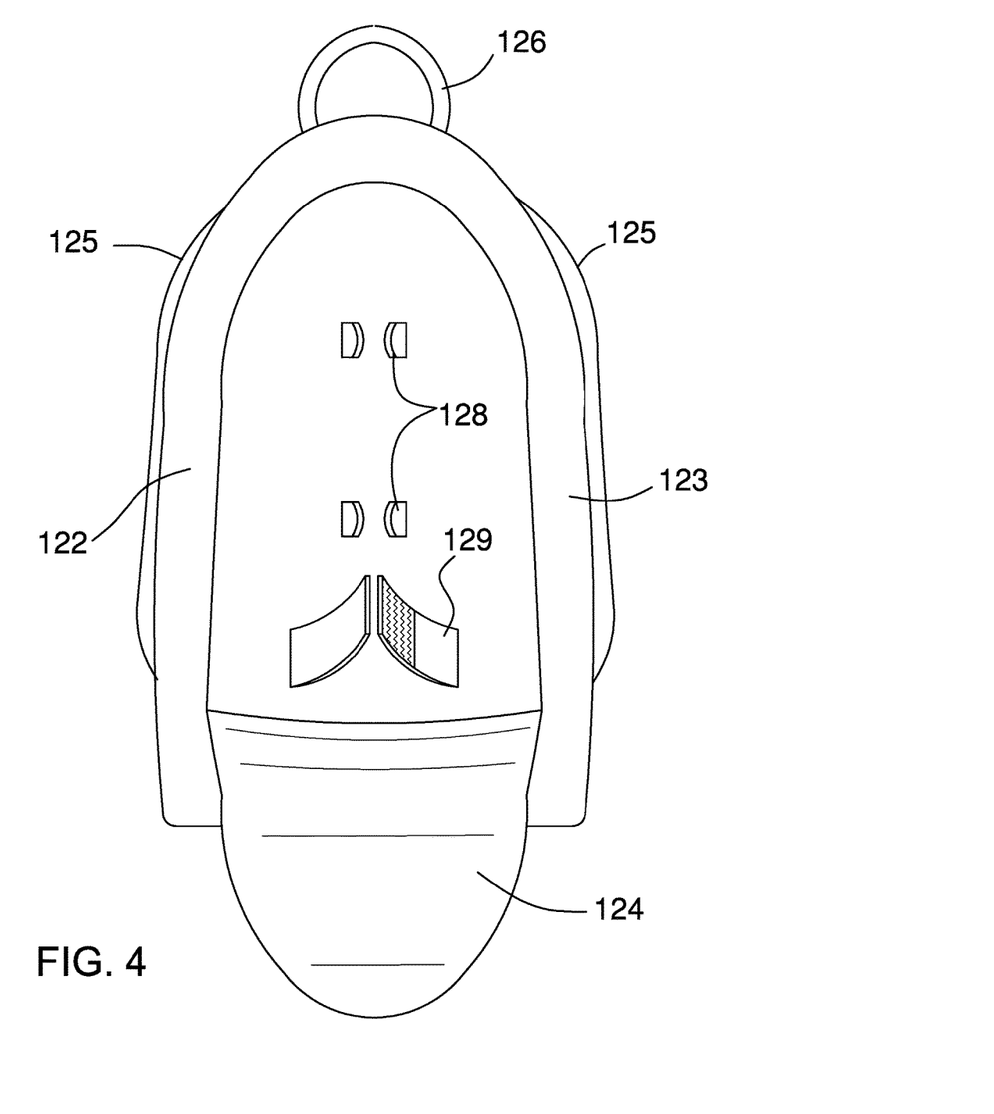
FIG. 4 is a posterior view of an embodiment of the disclosure.
Figure 5:
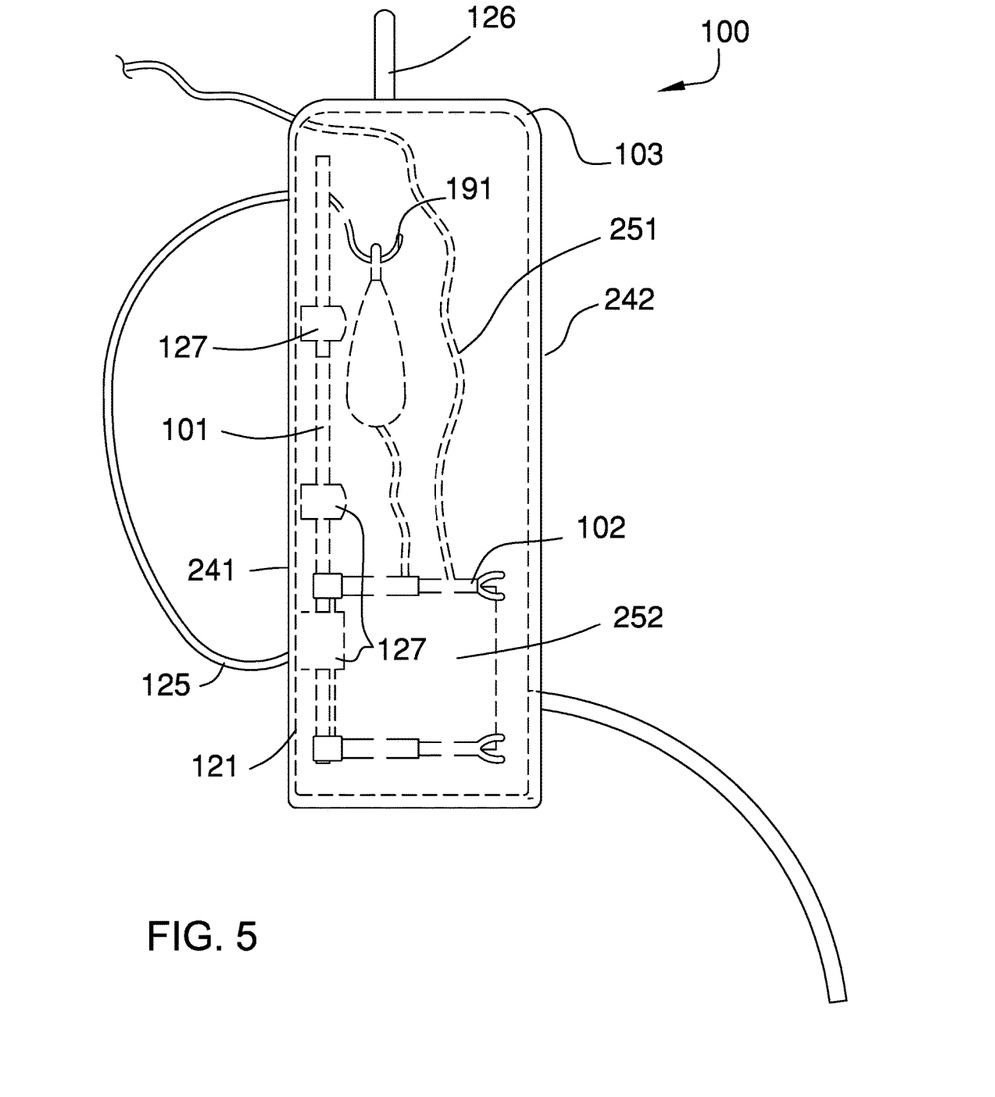
FIG. 5 is an in-use view of an embodiment of the disclosure.

Detailed reference will now be made to one or more potential embodiments of the disclosure, which are illustrated in FIGS. 1 through 5.

The enteral feeding system accessory 100 (hereinafter invention) is configured for use with an enteral feeding system. The enteral feeding system comprises a feeding tube 251 and a feeding machine 252. The feeding tube 251 is a gastric catheter. The feeding machine 252 is a pump and reservoir that pumps nutrition through the feeding tube 251 to a patient. The invention 100 is luggage item that is configured to transport the enteral feeding system. The invention 100 comprises a stanchion 101, a plurality of mounting brackets 102, and a backpack 103. The plurality of mounting brackets 102 attach to the stanchion 101. The stanchion 101 and plurality of mounting brackets 102 are attached to and contained within the backpack 103.

The stanchion 101 is a central shaft that forms the primary supporting structure of the invention 100. The stanchion 101 attaches the plurality of mounting brackets 102 to the backpack 103. The span of the length of the stanchion 101 is adjustable. The stanchion 101 forms a straight shaft-like structure. The stanchion 101 comprises a ninth telescopic structure 139.

The ninth telescopic structure 139 is a telescopic structure that comprises a seventeenth arm 177, an eighteenth arm 178, and a ninth detent 189. The ninth detent 189 attaches the seventeenth arm 177 to the eighteenth arm 178. The seventeenth arm 177 is a hollow prism that is further defined with an inner dimension. The eighteenth arm 178 is a prism that is further defined with an outer dimension. The eighteenth arm 178 is geometrically similar to the seventeenth arm 177. The span of the outer dimension of the eighteenth arm 178 is lesser than the span of the inner dimension of the seventeenth arm 177 such that the eighteenth arm 178 inserts into the seventeenth arm 177 in a telescopic fashion. This telescopic arrangement of the ninth telescopic structure 139 allows the length of the ninth telescopic structure 139 to be adjusted by adjusting the relative position of the eighteenth arm 178 within the seventeenth arm 177.

The position of the eighteenth arm 178 relative to the seventeenth arm 177 is held in position using the ninth detent 189. The ninth detent 189 is a mechanical device that locks and secures the eighteenth arm 178 to the seventeenth arm 177. The ninth detent 189 is selected from the group consisting of a cotter pin, a G snap collar, a cam lock collar, a threaded clutch, a split collar lock, or a spring loaded ball lock.

The seventeenth arm 177 is further defined with a thirty-third end 233 and a thirty-fourth end 234. The eighteenth arm 178 is further defined with a thirty-fifth end 235 and a thirty-sixth end 236.

Each of the plurality of mounting brackets 102 is a rectilinear structure that forms a right angle. Each of the plurality of mounting brackets 102 attaches to the stanchion 101. The span of the length of each of the plurality of mounting brackets 102 is adjustable in two dimensions. Each of the plurality of mounting brackets 102 is used to support and contain the feeding machine 252 within the backpack 103. The plurality of mounting brackets 102 comprises a first mounting bracket 111, a second mounting bracket 112, a third mounting bracket 113, and a fourth mounting bracket 114.

The first mounting bracket 111 is a mounting bracket selected from the plurality of mounting brackets 102. The first mounting bracket 111 holds the feeding machine 252 in a fixed position within the backpack 103. The first mounting bracket comprises a first telescopic structure 131, a second telescopic structure 132, a first 90-degree elbow 141, and a first gripping structure 151.

The first 90-degree elbow 141 is a commercially available hardware item that attaches first telescopic structure 131 to the second telescopic structure 132 to form a right angle. The first gripping structure 151 is a hook-like structure that is wrapped around the surface of the feeding machine 252 that is proximal to the posterior surface 242 of the backpack 103. The first gripping structure 151 secures the feeding machine 252 to the plurality of mounting brackets 102. The first gripping structure 151 is coated with an elastomeric material.

The first telescopic structure 131 is a telescopic structure that comprises a first arm 161, a second arm 162, and a first detent 181. The first detent 181 attaches the first arm to the second arm 162. The first arm 161 is a hollow tubular prism that is further defined with an inner dimension. The second arm 162 is a tubular prism that is further defined with an outer dimension. The second arm 162 is geometrically similar to the first arm 161. The span of the outer dimension of the second arm 162 is lesser than the span of the inner dimension of the first arm 161 such that the second arm 162 inserts into the first arm 161 in a telescopic fashion. This telescopic arrangement of the first telescopic structure 131 allows the length of the first telescopic structure 131 to be adjusted by adjusting the relative position of the second arm 162 within the first arm 161.

The position of the second arm 162 relative to the first arm 161 is held in position using the first detent 181. The first detent 181 is a mechanical device that locks and secures the second arm 162 to the first arm 161. The first detent 181 is selected from the group consisting of a cotter pin, a G snap collar, a cam lock collar, a threaded clutch, a split collar lock, or a spring loaded ball lock.

The second telescopic structure 132 is a telescopic structure that comprises a third arm 163, a fourth arm 164, and a second detent 182. The second detent 182 attaches the third arm 163 to the fourth arm 164. The third arm 163 is a hollow tubular prism that is further defined with an inner dimension. The fourth arm 164 is a tubular prism that is further defined with an outer dimension. The fourth arm 164 is geometrically similar to the third arm 163. The span of the outer dimension of the fourth arm 164 is lesser than the span of the inner dimension of the third arm 163 such that the fourth arm 164 inserts into the third arm 163 in a telescopic fashion. This telescopic arrangement of the second telescopic structure 132 allows the length of the second telescopic structure 132 to be adjusted by adjusting the relative position of the fourth arm within the third arm 163.

The position of the fourth arm 164 relative to the third arm 163 is held in position using the second detent 182. The second detent 182 is a mechanical device that locks and secures the fourth arm 164 to the third arm 163. The second detent 182 is selected from the group consisting of a cotter pin, a G snap collar, a cam lock collar, a threaded clutch, a split collar lock, or a spring loaded ball lock.

The first arm 161 is further defined with a first end 201 and a second end 202. The second arm 162 is further defined with a third end 203 and a fourth end 204. The third arm 163 is further defined with a fifth end 205 and a sixth end 206. The fourth arm 164 is further defined with a seventh end 207 and an eighth end 208.

The second mounting bracket 112 is a mounting bracket selected from the plurality of mounting brackets 102. The second mounting bracket 112 holds the feeding machine 252 in a fixed position within the backpack 103. The second mounting bracket 112 comprises a third telescopic structure 133, a fourth telescopic structure 134, a second 90-degree elbow 142, and a second gripping structure 152.

The second 90-degree elbow 142 is a commercially available hardware item that attaches the third telescopic structure 133 to the fourth telescopic structure 134 to form a right angle. The second gripping structure 152 is a hook-like structure that is wrapped around the surface of the feeding machine 252 that is proximal to the posterior surface 242 of the backpack 103. The second gripping structure 152 secures the feeding machine 252 to the plurality of mounting brackets 102. The second gripping structure 152 is coated with an elastomeric material.

The third telescopic structure 133 is a telescopic structure that comprises a fifth arm 165, a sixth arm 166, and a third detent 183. The third detent 183 attaches the fifth arm to the sixth arm 166. The fifth arm 165 is a hollow tubular prism that is further defined with an inner dimension. The sixth arm 166 is a tubular prism that is further defined with an outer dimension. The sixth arm 166 is geometrically similar to the fifth arm 165. The span of the outer dimension of the sixth arm 166 is lesser than the span of the inner dimension of the fifth arm 165 such that the sixth arm 166 inserts into the fifth arm 165 in a telescopic fashion. This telescopic arrangement of the third telescopic structure 133 allows the length of the third telescopic structure 133 to be adjusted by adjusting the relative position of the sixth arm 166 within the fifth arm 165.

The position of the sixth arm 166 relative to the fifth arm 165 is held in position using the third detent 183. The third detent 183 is a mechanical device that locks and secures the sixth arm 166 to the fifth arm 165. The third detent 183 is selected from the group consisting of a cotter pin, a G snap collar, a cam lock collar, a threaded clutch, a split collar lock, or a spring loaded ball lock.

The fourth telescopic structure 134 is a telescopic structure that comprises a seventh arm 167, an eighth arm 168, and a fourth detent 184. The fourth detent 184 attaches the seventh arm 167 to the eighth arm 168. The seventh arm 167 is a hollow tubular prism that is further defined with an inner dimension. The eighth arm 168 is a tubular prism that is further defined with an outer dimension. The eighth arm 168 is geometrically similar to the seventh arm 167. The span of the outer dimension of the eighth arm 168 is lesser than the span of the inner dimension of the seventh arm 167 such that the eighth arm 168 inserts into the seventh arm 167 in a telescopic fashion. This telescopic arrangement of the fourth telescopic structure 134 allows the length of the fourth telescopic structure 134 to be adjusted by adjusting the relative position of the eighth arm 168 within the seventh arm 167.

The position of the eighth arm 168 relative to the seventh arm 167 is held in position using the fourth detent 184. The fourth detent 184 is a mechanical device that locks and secures the eighth arm 168 to the seventh arm 167. The fourth detent is selected from the group consisting of a cotter pin, a G snap collar, a cam lock collar, a threaded clutch, a split collar lock, or a spring loaded ball lock.

The fifth arm 165 is further defined with a ninth end 209 and a tenth end 210. The sixth arm 166 is further defined with an eleventh end 211 and a twelfth end 212. The seventh arm 167 is further defined with a thirteenth end 213 and a fourteenth end 214. The eighth arm 168 is further defined with a fifteenth end 215 and a sixteenth end 216.

The third mounting bracket 113 is a mounting bracket selected from the plurality of mounting brackets 102. The third mounting bracket 113 holds the feeding machine 252 in a fixed position within the backpack 103. The third mounting bracket 113 comprises a fifth telescopic structure 135, a sixth telescopic structure 136, a third 90-degree elbow 143, and a third gripping structure 153.

The third 90-degree elbow 143 is a commercially available hardware item that attaches the fifth telescopic structure 135 to the sixth telescopic structure 136 to form a right angle. The third gripping structure 153 is a hook-like structure that is wrapped around the surface of the feeding machine 252 that is proximal to the posterior surface 242 of the backpack 103. The third gripping structure 153 secures the feeding machine 252 to the plurality of mounting brackets 102. The third gripping structure 153 is coated with an elastomeric material.

The fifth telescopic structure 135 is a telescopic structure that comprises a ninth arm 169, a tenth arm 170, and a fifth detent 185. The fifth detent 185 attaches the ninth arm 169 to the tenth arm 170. The ninth arm 169 is a hollow tubular prism that is further defined with an inner dimension. The tenth arm 170 is a tubular prism that is further defined with an outer dimension. The tenth arm 170 is geometrically similar to the ninth arm 169. The span of the outer dimension of the tenth arm 170 is lesser than the span of the inner dimension of the ninth arm 169 such that the tenth arm 170 inserts into the ninth arm 169 in a telescopic fashion. This telescopic arrangement of the fifth telescopic structure 135 allows the length of the fifth telescopic structure 135 to be adjusted by adjusting the relative position of the tenth arm 170 within the ninth arm 169.

The position of the tenth arm 170 relative to the ninth arm 169 is held in position using the fifth detent 185. The fifth detent 185 is a mechanical device that locks and secures the tenth arm 170 to the ninth arm 169. The fifth detent 185 is selected from the group consisting of a cotter pin, a G snap collar, a cam lock collar, a threaded clutch, a split collar lock, or a spring loaded ball lock.

The sixth telescopic structure 136 is a telescopic structure that comprises an eleventh arm 171, a twelfth arm 172, and a sixth detent 186. The sixth detent 186 attaches the eleventh arm 171 to the twelfth arm 172. The eleventh arm 171 is a hollow tubular prism that is further defined with an inner dimension. The twelfth arm 172 is a tubular prism that is further defined with an outer dimension. The twelfth arm 172 is geometrically similar to the eleventh arm 171. The span of the outer dimension of the twelfth arm 172 is lesser than the span of the inner dimension of the eleventh arm 171 such that the twelfth arm 172 inserts into the eleventh arm 171 in a telescopic fashion. This telescopic arrangement of the sixth telescopic structure 136 allows the length of the sixth telescopic structure 136 to be adjusted by adjusting the relative position of the twelfth arm 172 within the eleventh arm 171.

The position of the twelfth arm 172 relative to the eleventh arm 171 is held in position using the sixth detent 186. The sixth detent 186 is a mechanical device that locks and secures the twelfth arm 172 to the eleventh arm 171. The sixth detent 186 is selected from the group consisting of a cotter pin, a G snap collar, a cam lock collar, a threaded clutch, a split collar lock, or a spring loaded ball lock.

The ninth arm 169 is further defined with a seventeenth end 217 and an eighteenth end 218. The tenth arm 170 is further defined with a nineteenth end 219 and a twentieth end 220. The eleventh arm 171 is further defined with a twenty-first end 221 and a twenty-second end 222. The twelfth arm 172 is further defined with a twenty-third end 223 and a twenty-fourth end 224.

The fourth mounting bracket 114 is a mounting bracket selected from the plurality of mounting brackets 102. The fourth mounting bracket 114 holds the feeding machine 252 in a fixed position within the backpack 103. The fourth mounting bracket 114 comprises a seventh telescopic structure 137, an eighth telescopic structure 138, a fourth 90-degree elbow 144, and a fourth gripping structure 154.

The fourth 90-degree elbow 144 is a commercially available hardware item that attaches the seventh telescopic structure 137 to the eighth telescopic structure 138 to form a right angle. The fourth gripping structure 154 is a hook-like structure that is wrapped around the surface of the feeding machine 252 that is proximal to the posterior surface 242 of the backpack 103. The fourth gripping structure 154 secures the feeding machine 252 to the plurality of mounting brackets 102. The fourth gripping structure 154 is coated with an elastomeric material.

The seventh telescopic structure 137 is a telescopic structure that comprises a thirteenth arm 173, a fourteenth arm 174, and a seventh detent 187. The seventh detent 187 attaches the thirteenth arm 173 to the fourteenth arm 174. The thirteenth arm 173 is a hollow tubular prism that is further defined with an inner dimension. The fourteenth arm 174 is a tubular prism that is further defined with an outer dimension. The fourteenth arm 174 is geometrically similar to the thirteenth arm 173. The span of the outer dimension of the fourteenth arm 174 is lesser than the span of the inner dimension of the thirteenth arm 173 such that the fourteenth arm 174 inserts into the thirteenth arm 173 in a telescopic fashion. This telescopic arrangement of the seventh telescopic structure 137 allows the length of the seventh telescopic structure 137 to be adjusted by adjusting the relative position of the fourteenth arm 174 within the thirteenth arm 173.

The position of the fourteenth arm 174 relative to the thirteenth arm 173 is held in position using the seventh detent 187. The seventh detent 187 is a mechanical device that locks and secures the fourteenth arm 174 to the thirteenth arm 173. The seventh detent 187 is selected from the group consisting of a cotter pin, a G snap collar, a cam lock collar, a threaded clutch, a split collar lock, or a spring loaded ball lock.

The eighth telescopic structure 138 is a telescopic structure that comprises a fifteenth arm 175, a sixteenth arm 176, and an eighth detent 188. The eighth detent 188 attaches the fifteenth arm 175 to the sixteenth arm 176. The fifteenth arm 175 is a hollow tubular prism that is further defined with an inner dimension. The sixteenth arm 176 is a hollow tubular prism that is further defined with an outer dimension. The sixteenth arm 176 is geometrically similar to the fifteenth arm 175. The span of the outer dimension of the sixteenth arm 176 is lesser than the span of the inner dimension of the fifteenth arm 175 such that the sixteenth arm 176 inserts into the fifteenth arm 175 in a telescopic fashion. This telescopic arrangement of the eighth telescopic structure 138 allows the length of the eighth telescopic structure 138 to be adjusted by adjusting the relative position of the sixteenth arm 176 within the fifteenth arm 175.

The position of the sixteenth arm 176 relative to the fifteenth arm 175 is held in position using the eighth detent 188. The eighth detent 188 is a mechanical device that locks and secures the sixteenth arm 176 to the fifteenth arm 175. The eighth detent 188 is selected from the group consisting of a cotter pin, a G snap collar, a cam lock collar, a threaded clutch, a split collar lock, or a spring loaded ball lock.

The thirteenth arm 173 is further defined with a twenty-fifth end 225 and a twenty-sixth end 226. The fourteenth arm 174 is further defined with a twenty-seventh end 227 and a twenty-eighth end 228. The fifteenth arm 175 is further defined with a twenty-ninth end 229 and a thirtieth end 230. The sixteenth arm 176 is further defined with a thirty-first end 231 and a thirty-second end 232.

In a second potential embodiment of the disclosure, the plurality of mounting brackets 102 further comprises a plurality of miscellaneous brackets 104. The plurality of miscellaneous brackets 104 comprises a pump support 301 and a plurality of yoke clamps 310. The plurality of yoke clamps 310 further comprises an upper yoke clamp 311 and a lower yoke clamp 312.

The pump support 301 is a prism structure that is geometrically similar to the seventeenth arm 177. The pump support 301 attaches to the seventeenth arm 177 proximal to the thirty third end 233 in the manner of a cantilever. The span of the length of the pump support 301 is lesser than or equal to the span of the length of the eighth telescopic structure 138. The pump support 301 projects perpendicularly away from the seventeenth arm 177 is the direction of and parallel to the eighth telescopic structure 138. The feeding machine 252 attaches to the pump 301 support.

The upper yoke clamp 311 further comprises a first yoke shaft 313 and a first terry clip 3. The first yoke shaft 313 is a shaft that is geometrically similar to the seventeenth arm 177. The first yoke shaft 313 removably attaches to the seventeenth arm 177. The first yoke shaft 313 projects away from the seventeenth arm 177 in a direction that is: 1) perpendicular to the seventeenth arm 177; and, 2) opposite to the direction of the pump support 301. The first terry clip 314 attaches to the free end of the first yoke shaft 313. The first terry clip 314 is a commercially available terry clip that attaches the shaft-like structures commonly found on objects including, but not limited to, wheelchairs, walkers, strollers, and bedposts.

The lower yoke clamp 312 further comprises a second yoke shaft 315 and a second terry clip 316. The second yoke shaft 315 is a shaft that is geometrically similar to the seventeenth arm 177. The second yoke shaft 315 removably attaches to the seventeenth arm 177. The second yoke shaft 315 projects away from the seventeenth arm 177 in a direction that is: 1) perpendicular to the seventeenth arm 177; and, 2) opposite to the direction of the pump support 301. The second terry clip 316 attaches to the free end of the second yoke shaft 315. The second terry clip 316 is a commercially available terry clip that attaches the shaft-like structures commonly found on objects including, but not limited to, wheelchairs, walkers, strollers, and bedposts.

The backpack 103 is a luggage item. The backpack 103 is used to contain the enteral feeding system during transportation. The backpack 103 comprises an anterior plate 121, a left panel 122, a right panel 123, a lid 124, a plurality of shoulder straps 125, a handle loop 126, and a plurality of clasps 127.

The anterior plate 121 is a rigid structure that forms the anterior surface 241 of the backpack 103. The stanchion 101 and the plurality of mounting brackets 102 are attached to the anterior plate 121. The rigidity of the anterior plate 121 protects the feeding machine 252 from shifts in orientation relative to the force of gravity when the feeding machine 252 is stored in the backpack 103.

The left panel 122 is a textile sheeting. The left panel 122 attaches to the right panel 123 and the anterior plate 121 to form the containment area of the backpack 103. The right panel 123 is a textile sheeting. The right panel 123 attaches to the left panel 122 and the anterior plate 121 to form the containment area of the backpack 103. The lid 124 is a textile sheeting. The lid 124 covers the opening through the posterior surface 242 of the backpack 103 that provides access to the containment area of the backpack 103.

The plurality of shoulder straps 125 is a harness that attaches the backpack 103 to a person. The handle loop 126 is a grip that allows the backpack 103 to be hand carried.

Each of the plurality of clasps 127 is a fastening device that attaches the stanchion 101 to the anterior plate 121. Each of the plurality of clasps 127 is a fastening device selected from the group consisting of a cantilever spring 128 and a hook and loop fastener 129. The cantilever spring 128 is a well-known and documented fastening device known as a cantilever V spring. The cantilever V spring is described in greater detail elsewhere in this disclosure. The hook and loop fastener 129 is a well-known and documented fastening device. The hook and loop fastener 129 is described in greater detail elsewhere in this disclosure.

The following seven paragraphs describe the assembly of the stanchion 101 and the plurality of mounting brackets 102.

The thirty-fifth end 235 of the eighteenth arm 178 inserts into the thirty-fourth end 234 of the seventeenth arm 177 to form the ninth telescopic structure 139. The hook 191 attaches to the eighteenth arm 178 at a location proximal to the thirty-sixth end 236. The plurality of clasps 127 attaches the ninth telescopic structure 139 to the anterior plate 121.

The eighth end 208 of the fourth arm 164 attaches to the seventeenth arm 177 of the ninth telescopic structure 139 such that the fourth arm 164 projects perpendicularly away from the seventeenth arm 177. The twelfth end 212 of the sixth arm 166 attaches to the seventeenth arm 177 of the ninth telescopic structure 139 such that the sixth arm 166 projects perpendicularly away from the seventeenth arm 177. The twenty-fourth end 224 of the twelfth arm 172 attaches to the seventeenth arm 177 of the ninth telescopic structure 139 such that the twelfth arm 172 projects perpendicularly away from the seventeenth arm 177. The twenty-eighth end 228 of the fourteenth arm 174 attaches to the seventeenth arm 177 of the ninth telescopic structure 139 such that the fourteenth arm 174 projects perpendicularly away from the seventeenth arm 177.

The seventh end 207 of the fourth arm 164 inserts into the sixth end 206 of the third arm 163 to form the second telescopic structure 132. The first 90-degree elbow 141 attaches the fifth end 205 of the third arm 163 to the first end 201 of the first arm 161 to form a right angle. The third end 203 of the second arm 162 inserts into the second end 202 of the first arm 161 to form the first telescopic structure 131.

The eleventh end 211 of the sixth arm 166 inserts into the tenth end 210 of the fifth arm 165 to form the third telescopic structure 133. The second 90-degree elbow 142 attaches the ninth end 209 of the fifth arm 165 to the thirteenth end 213 of the seventh arm 167 to form a right angle. The fifteenth end 215 of the eighth arm 168 inserts into the fourteenth end 214 of the seventh arm 167 to form the fourth telescopic structure 134.

The twenty-third end 223 of the twelfth arm 172 inserts into the twenty-second end 222 of the eleventh arm 171 to form the sixth telescopic structure 136. The third 90-degree elbow 143 attaches the twenty-first end 221 of the eleventh arm 171 to the seventeenth end 217 of the ninth arm 169 to form a right angle. The nineteenth end 219 of the tenth arm 170 inserts into the eighteenth end 218 of the ninth arm 169 to form the fifth telescopic structure 135.

The twenty-seventh end 227 of the fourteenth arm 174 inserts into the twenty-sixth end 226 of the thirteenth arm 173 to form the seventh telescopic structure 137. The fourth 90-degree elbow 144 attaches the twenty-fifth end 225 of the thirteenth arm 173 to the twenty-ninth end 229 of the fifteenth arm 175 to form a right angle. The thirty-first end 231 of the sixteenth arm 176 inserts into the thirtieth end 230 of the fifteenth arm 175 to form the eighth telescopic structure 138.

The first gripping structure 151 attaches to the fourth end of the second arm 162. The second gripping structure 152 attaches to the sixteenth end 216 of the eighth arm 168. The third gripping structure 153 attaches to the twentieth end 220 of the tenth arm 170. The fourth gripping structure 154 attaches to the thirty-second end 232 of the sixteenth arm 176.

This paragraph describes the assembly of the backpack 103. The anterior plate 121 forms the anterior surface 241 of the backpack 103. The left panel 122 and the right panel 123 are used to enclose the perimeter of the anterior plate 121 such that a containment area is formed. The containment area is formed such that access to the containment area is through the posterior surface 242 of the backpack 103. The containment area of the backpack 103 is enclosed using the lid 124. In the first potential embodiment of the disclosure, the lid 124 fastens to the left panel 122 and the right panel 123 using a zipper. The plurality of clasps 127 attach to the anterior plate 121 such that the plurality of clasps 127 are accessible from the interior of the backpack 103. The plurality of shoulder straps 125 and the handle loop 126 using traditional methods for assembling luggage.

This paragraph describes the use of the invention 100. The span of the lengths of each of the first telescopic structure 131, the second telescopic structure 132, the third telescopic structure 133, the fourth telescopic structure 134, the fifth telescopic structure 135, the sixth telescopic structure 136, the seventh telescopic structure 137, and the eighth telescopic structure 138 are set to form a framing area in the shape of a rectangular block. The framing area is sized such that the plurality of mounting brackets 102 will support the feeding machine 252 within the backpack 103. As shown most clearly in FIG. 5, the span of the length of the ninth telescopic structure 139 is set such that a bag containing nutrition can be supported from the hook 191 above the feeding tube 251.

The following definitions were used in this disclosure:

90-Degree Elbow: As used in this disclosure, a 90-degree elbow is a two aperture fitting that attaches a first pipe to a second pipe such that the center axis of the first pipe is perpendicular to the center axis of the second pipe.

Anterior: As used in this disclosure, anterior is a term that is used to refer to the front side or direction of a structure. When comparing two objects, the anterior object is the object that is closer to the front of the structure.

Backpack: As used in this disclosure, a backpack is an item of luggage that comprises a harness arrangement that allows the backpack to be carried on the back of a user. The harness arrangement commonly comprises a plurality of shoulder straps.

Bracket: As used in this disclosure, a bracket is a mechanical structure that attaches a second structure to a first structure such that the load path of the second structure is fully transferred to the first structure.

Cantilever: As used in this disclosure, a cantilever is a beam or other structure that projects away from an object and is supported on only one end. A cantilever is further defined with a fixed end and a free end. The fixed end is the end of the cantilever that is attached to the object. The free end is the end of the cantilever that is distal from the fixed end.

Cantilever V Spring: As used in this disclosure, a cantilever V spring is a torsion spring that is formed in a chevron shape. The cantilever V spring comprises a first cantilever structure and a second cantilever structure wherein the fixed end of the first cantilever structure is attached to the fixed end of the second cantilever structure. Within this structure, when a force is applied to the cantilever V spring such that the first cantilever structure moves relative to from the second cantilever structure the force deforms the cantilever V spring in an elastic manner that: 1) resists the application of the force; and 2) stores the energy deformation such that when the force is no longer applied the cantilever V spring returns to its relaxed shape. Depending on the application, a cantilever V spring can be considered a torsion spring, a tension spring, or a compression spring.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Chevron: As used in this disclosure, chevron is a term that is used to describe an object that has the shape of a U or a V.

Clip: As used in this disclosure, a clip is a fastener that attaches to an object by gripping or clasping the object. A clip is typically spring loaded.

Correspond: As used in this disclosure, the term correspond is used as a comparison between two or more objects wherein one or more properties shared by the two or more objects match, agree, or align within acceptable manufacturing tolerances.

Detent: As used in this disclosure, a detent is a device for positioning and holding a first object relative to a second object such that the position of the first object relative to the second object is adjustable.

Elastic: As used in this disclosure, an elastic is a material or object that deforms when a force is applied to it and that is able to return to its relaxed shape after the force is removed. A material that exhibits these qualities is also referred to as an elastomeric material.

Force of Gravity: As used in this disclosure, the force of gravity refers to a vector that indicates the direction of the pull of gravity on an object at or near the surface of the earth.

Gastric Catheter: As used in this disclosure, a gastric catheter refers to what is commonly called a feeding tube that is inserted into the esophagus to provide nutrition to a patient.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Hook: As used in this disclosure, a hook is an object that is curved or bent at an angle such that items can be hung on or caught by the object.

Hook and Loop Fastener: As used in this disclosure, a hook and loop fastener is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface. A note on usage: when fastening two objects the hook surface of a hook and loop fastener will be placed on the first object and the matching loop surface of a hook and loop fastener will be placed on the second object without significant regard to which object of the two objects is the first object and which of the two objects is the second object. When the hook surface of a hook and loop fastener or the loop surface of a hook and loop fastener is attached to an object this will simply be referred to as the "hook/loop surface" with the understanding that when the two objects are fastened together one of the two objects will have a hook surface and the remaining object will have the loop surface.

Inferior: As used in this disclosure, the term inferior refers to a directional reference that is parallel to and in the same direction as the force of gravity.

Inner Dimension: As used in this disclosure, the term inner dimension describes the span from a first inside or interior surface of a container to a second inside or interior surface of a container. The term is used in much the same way that a plumber would refer to the inner diameter of a pipe.

Lid: As used in this disclosure, a lid is a removable cover that is placed over an opening of a hollow structure to enclose the hollow structure.

Load Path: As used in this disclosure, a load path refers to a chain of one or more structures that transfers a load generated by a raised structure or object to a foundation, supporting surface, or the earth.

Luggage: As used in this disclosure, luggage is a trunk, bag, parcel, suitcase, or backpack in which domestic articles are contained during travel.

One to One: When used in this disclosure, a one to one relationship means that a first element selected from a first set is in some manner connected to only one element of a second set. A one to one correspondence means that the one to one relationship exists both from the first set the second set and from the second set to the first set. A one to one fashion means that the one to one relationship exists in only one direction.

Orientation: As used in this disclosure, orientation refers to the positioning of a first object relative to: 1) a second object; or, 2) a fixed position, location, or direction.

Outer Dimension: As used in this disclosure, the term outer dimension describes the span from a first exterior or outer surface of a tube or container to a second exterior or outer surface of a tube or container. The term is used in much the same way that a plumber would refer to the outer diameter of a pipe.

Patient: As used in this disclosure, a patient is a person who is designated to receive a medical treatment, therapy or service. The term patient may be extended to an animal when used within the context of the animal receiving veterinary treatment or services Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Posterior: As used in this disclosure, posterior is a term that is used to refer to the side of an object that is distal or in the opposite direction of the anterior side. When comparing two items, the posterior item is the item that is distal from the front of the object.

Rigid Structure: As used in this disclosure, a rigid structure is a solid structure formed from an inelastic material that resists changes in shape. A rigid structure will permanently deform as it fails under a force.

Sheeting: As used in this disclosure, a sheeting is a material, such as a textile, a plastic, or a metal foil, in the form of a thin flexible layer or layers.

Spring: As used in this disclosure, a spring is a device that is used to store mechanical energy. This mechanical energy will often be stored by: 1) deforming an elastomeric material that is used to make the device; 2) the application of a torque to a rigid structure; or 3) a combination of the previous two items.

Stanchion: As used in this disclosure, a stanchion refers to a vertical pole, post, or support.

Strap: As used in this disclosure a strap is a strip of leather, cloth, or other flexible material, often with a buckle, that is used to fasten, secure, carry, or hold onto something.

Superior: As used in this disclosure, the term superior refers to a directional reference that is parallel to and in the opposite direction of the force of gravity.

Telescopic: As used in this disclosure, telescopic is an adjective that describes an object made of sections that fit or slide into each other such that the object can be made longer or shorter by adjusting the relative positions of the sections.

Terry Clip: As used in this disclosure, a terry clip is a hyoid shaped version of a cantilever V spring that is commonly used to attach the handle of a tool to a vertical surface.

Textile: As used in this disclosure, a textile is a material that is woven, knitted, braided or felted. Synonyms in common usage for this definition include fabric and cloth.

Tube: As used in this disclosure, the term tube is used to describe a rigid hollow prism. While tubes that are suitable for use in this disclosure are often used to transport or conveys fluids or gases, the purpose of the tubes in this disclosure are structural. In this disclosure, the terms inner dimension and outer dimension of a tube are used as they would be used by those skilled in the plumbing arts.

Zipper: As used in this disclosure, a zipper is a fastening device comprising two flexible strips with interlocking components that are opened and closed by pulling a slide along the two flexible strips.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A therapeutic accessory comprising:
   a stanchion, a plurality of mounting brackets, and a backpack;
   wherein the plurality of mounting brackets attach to the stanchion;
   wherein the stanchion and plurality of mounting brackets are attached to and contained within the backpack;
   wherein the therapeutic accessory is configured for use with an enteral feeding system;
   wherein the enteral feeding system comprises a feeding tube and a feeding machine;
   wherein the therapeutic accessory is a luggage item that is configured to transport the enteral feeding system;
   wherein the stanchion attaches the plurality of mounting brackets to the backpack;
   wherein the stanchion comprises a ninth telescopic structure;
   wherein each of the plurality of mounting brackets is a rectilinear structure that forms a right angle;
   wherein each of the plurality of mounting brackets attaches to the stanchion;
   wherein the span of the length of each of the plurality of mounting brackets is adjustable in two dimensions;
   wherein each of the plurality of mounting brackets is used to support and contain the feeding machine within the backpack;
   wherein the plurality of mounting brackets comprises a first mounting bracket, a second mounting bracket, a third mounting bracket, and a fourth mounting bracket;
   wherein the backpack is a luggage item that is further defined with an anterior surface and a posterior surface;
   wherein the ninth telescopic structure is a telescopic structure that comprises a seventeenth arm, an eighteenth arm, and a ninth detent;
   wherein the position of the eighteenth arm relative to the seventeenth arm is held in position using the ninth detent;
   wherein the seventeenth arm is a hollow prism that is further defined with an inner dimension;
   wherein the eighteenth arm is a prism that is further defined with an outer dimension;
   wherein the eighteenth arm is geometrically similar to the seventeenth arm;
   wherein the span of the outer dimension of the eighteenth arm is lesser than the span of the inner dimension of the seventeenth arm such that the eighteenth arm inserts into the seventeenth arm;
   wherein the length of the ninth telescopic structure is adjusted by adjusting the relative position of the eighteenth arm within the seventeenth arm;
   wherein the seventeenth arm is further defined with a thirty-third end and a thirty-fourth end;
   wherein the eighteenth arm is further defined with a thirty-fifth end and a thirty-sixth end.

2. The therapeutic accessory according to claim 1
   wherein the first mounting bracket comprises a first telescopic structure, a second telescopic structure, a first 90-degree elbow, and a first gripping structure;
   wherein the first 90-degree elbow attaches first telescopic structure to the second telescopic structure to form a right angle;
   wherein the first gripping structure is a hook-like structure;
   wherein the second mounting bracket comprises a third telescopic structure, a fourth telescopic structure, a second 90-degree elbow, and a second gripping structure;
   wherein the second 90-degree elbow attaches the third telescopic structure to the fourth telescopic structure to form a right angle;
   wherein the second gripping structure is a hook-like structure;
   wherein the third mounting bracket comprises a fifth telescopic structure, a sixth telescopic structure, a third 90-degree elbow, and a third gripping structure;
   wherein the third 90-degree elbow attaches the fifth telescopic structure to the sixth telescopic structure to form a right angle;
   wherein the third gripping structure is a hook-like structure;

wherein the fourth mounting bracket comprises a seventh telescopic structure, an eighth telescopic structure, a fourth 90-degree elbow, and a fourth gripping structure;
wherein the fourth 90-degree elbow attaches the seventh telescopic structure to the eighth telescopic structure to form a right angle;
wherein the fourth gripping structure is a hook-like structure.

3. The therapeutic accessory according to claim 2
wherein the first telescopic structure is a telescopic structure that comprises a first arm, a second arm, and a first detent;
wherein the first detent attaches the first arm to the second arm;
wherein the first arm is a hollow tubular prism that is further defined with an inner dimension;
wherein the first detent is a mechanical device;
wherein the second arm is a tubular prism that is further defined with an outer dimension;
wherein the second arm is geometrically similar to the first arm;
wherein the second telescopic structure is a telescopic structure that comprises a third arm, a fourth arm, and a second detent;
wherein the second detent attaches the third arm to the fourth arm;
wherein the third arm is a hollow tubular prism that is further defined with an inner dimension;
wherein the fourth arm is a tubular prism that is further defined with an outer dimension;
wherein the fourth arm is geometrically similar to the third arm;
wherein the second detent is a mechanical device;
wherein the third telescopic structure is a telescopic structure that comprises a fifth arm, a sixth arm, and a third detent;
wherein the third detent attaches the fifth arm to the sixth arm;
wherein the fifth arm is a hollow tubular prism that is further defined with an inner dimension;
wherein the sixth arm is a tubular prism that is further defined with an outer dimension;
wherein the sixth arm is geometrically similar to the fifth arm;
wherein the third detent is a mechanical device;
wherein the fourth telescopic structure is a telescopic structure that comprises a seventh arm, an eighth arm, and a fourth detent;
wherein the fourth detent attaches the seventh arm to the eighth arm;
wherein the seventh arm is a hollow tubular prism that is further defined with an inner dimension;
wherein the eighth arm is a tubular prism that is further defined with an outer dimension;
wherein the eighth arm is geometrically similar to the seventh arm;
wherein the fourth detent is a mechanical device;
wherein the fifth telescopic structure is a telescopic structure that comprises a ninth arm, a tenth arm, and a fifth detent;
wherein the fifth detent attaches the ninth arm to the tenth arm;
wherein the ninth arm is a hollow tubular prism that is further defined with an inner dimension;
wherein the tenth arm is a tubular prism that is further defined with an outer dimension;
wherein the tenth arm is geometrically similar to the ninth arm;
wherein the fifth detent is a mechanical device;
wherein the sixth telescopic structure is a telescopic structure that comprises an eleventh arm, a twelfth arm, and a sixth detent;
wherein the sixth detent attaches the eleventh arm to the twelfth arm;
wherein the eleventh arm is a hollow tubular prism that is further defined with an inner dimension;
wherein the twelfth arm is a tubular prism that is further defined with an outer dimension;
wherein the twelfth arm is geometrically similar to the eleventh arm;
wherein the sixth detent is a mechanical device;
wherein the seventh telescopic structure is a telescopic structure that comprises a thirteenth arm, a fourteenth arm, and a seventh detent;
wherein the seventh detent attaches the thirteenth arm to the fourteenth arm;
wherein the thirteenth arm is a hollow tubular prism that is further defined with an inner dimension;
wherein the fourteenth arm is a tubular prism that is further defined with an outer dimension;
wherein the fourteenth arm is geometrically similar to the thirteenth arm;
wherein the seventh detent is a mechanical device;
wherein the eighth telescopic structure is a telescopic structure that comprises a fifteenth arm, a sixteenth arm, and an eighth detent;
wherein the eighth detent attaches the fifteenth arm to the sixteenth arm;
wherein the fifteenth arm is a hollow tubular prism that is further defined with an inner dimension;
wherein the sixteenth arm is a hollow tubular prism that is further defined with an outer dimension;
wherein the sixteenth arm is geometrically similar to the fifteenth arm;
wherein the eighth detent is a mechanical device;
wherein the first arm is further defined with a first end and a second end;
wherein the second arm is further defined with a third end and a fourth end;
wherein the third arm is further defined with a fifth end and a sixth end;
wherein the fourth arm is further defined with a seventh end and an eighth end;
wherein the fifth arm is further defined with a ninth end and a tenth end;
wherein the sixth arm is further defined with an eleventh end and a twelfth end;
wherein the seventh arm is further defined with a thirteenth end and a fourteenth end;
wherein the eighth arm is further defined with a fifteenth end and a sixteenth end;
wherein the ninth arm is further defined with a seventeenth end and an eighteenth end;
wherein the tenth arm is further defined with a nineteenth end and a twentieth end;
wherein the eleventh arm is further defined with a twenty-first end and a twenty-second end;
wherein the twelfth arm is further defined with a twenty-third end and a twenty-fourth end;
wherein the thirteenth arm is further defined with a twenty-fifth end and a twenty-sixth end;
wherein the fourteenth arm is further defined with a twenty-seventh end and a twenty-eighth end;

wherein the fifteenth arm is further defined with a twenty-ninth end and a thirtieth end;
wherein the sixteenth arm is further defined with a thirty-first end and a thirty-second end.

4. The therapeutic accessory according to claim 3
wherein the span of the outer dimension of the second arm is lesser than the span of the inner dimension of the first arm such that the second arm inserts into the first arm;
wherein the span of the outer dimension of the sixth arm is lesser than the span of the inner dimension of the fifth arm such that the sixth arm inserts into the fifth arm;
wherein the span of the outer dimension of the fourth arm is lesser than the span of the inner dimension of the third arm such that the fourth arm inserts into the third arm;
wherein the span of the outer dimension of the eighth arm is lesser than the span of the inner dimension of the seventh arm such that the eighth arm inserts into the seventh arm;
wherein the span of the outer dimension of the tenth arm is lesser than the span of the inner dimension of the ninth arm such that the tenth arm inserts into the ninth arm;
wherein the span of the outer dimension of the twelfth arm is lesser than the span of the inner dimension of the eleventh arm such that the twelfth arm inserts into the eleventh arm;
wherein the span of the outer dimension of the fourteenth arm is lesser than the span of the inner dimension of the thirteenth arm such that the fourteenth arm inserts into the thirteenth arm;
wherein the span of the outer dimension of the sixteenth arm is lesser than the span of the inner dimension of the fifteenth arm such that the sixteenth arm inserts into the fifteenth arm.

5. The therapeutic accessory according to claim 4
wherein the length of the first telescopic structure is adjusted by adjusting the relative position of the second arm within the first arm;
wherein the length of the second telescopic structure is adjusted by adjusting the relative position of the fourth arm within the third arm;
wherein the third telescopic structure is adjusted by adjusting the relative position of the sixth arm within the fifth arm;
wherein the length of the fourth telescopic structure is by adjusting the relative position of the eighth arm within the seventh arm;
wherein the length of the fifth telescopic structure is adjusted by adjusting the relative position of the tenth arm within the ninth arm;
wherein the length of the sixth telescopic structure is adjusted by adjusting the relative position of the twelfth arm within the eleventh arm;
wherein the length of the seventh telescopic structure to be adjusted by adjusting the relative position of the fourteenth arm within the thirteenth arm;
wherein the eighth telescopic structure is adjusted by adjusting the relative position of the sixteenth arm within the fifteenth arm.

6. The therapeutic accessory according to claim 5
wherein the backpack comprises an anterior plate, a left panel, a right panel, a lid, a plurality of shoulder straps, a handle loop, and a plurality of clasps;
wherein the anterior plate, the left panel, the right panel, the lid, the plurality of shoulder straps, and the handle loop are interconnected;
wherein the plurality of clasps attach to the anterior plate.

7. The therapeutic accessory according to claim 6
wherein the anterior plate is a rigid structure;
wherein the anterior plate forms the anterior surface of the backpack;
wherein each of the plurality of clasps is a fastening device that attaches the stanchion to the anterior plate.

8. The therapeutic accessory according to claim 7
wherein the left panel is a textile sheeting;
wherein the right panel is a textile sheeting;
wherein the left panel attaches to the right panel and the anterior plate to form the containment area of the backpack;
wherein the right panel attaches to the left panel and the anterior plate to form the containment area of the backpack.

9. The therapeutic accessory according to claim 8
wherein the lid is a textile sheeting;
wherein the lid covers an opening through the posterior surface of the backpack.

10. The therapeutic accessory according to claim 9
wherein the plurality of shoulder straps is a harness;
wherein the handle loop is a grip.

11. The therapeutic accessory according to claim 10 wherein each of the plurality of clasps is a fastening device selected from the group consisting of a cantilever spring and a hook and loop fastener.

12. The therapeutic accessory according to claim 11
wherein the thirty-fifth end of the eighteenth arm inserts into the thirty-fourth end of the seventeenth arm to form the ninth telescopic structure;
wherein the hook attaches to the eighteenth arm at a location proximal to the thirty-sixth end;
wherein the plurality of clasps attaches the ninth telescopic structure to the anterior plate;
wherein the eighth end of the fourth arm attaches to the seventeenth arm of the ninth telescopic structure such that the fourth arm projects perpendicularly away from the seventeenth arm;
wherein the twelfth end of the sixth arm attaches to the seventeenth arm of the ninth telescopic structure such that the sixth arm projects perpendicularly away from the seventeenth arm;
wherein the twenty-fourth end of the twelfth arm attaches to the seventeenth arm of the ninth telescopic structure such that the twelfth arm projects perpendicularly away from the seventeenth arm;
wherein the twenty-eighth end of the fourteenth arm attaches to the seventeenth arm of the ninth telescopic structure such that the fourteenth arm projects perpendicularly away from the seventeenth arm.

13. The therapeutic accessory according to claim 12
wherein the seventh end of the fourth arm inserts into the sixth end of the third arm to form the second telescopic structure;
wherein the first 90-degree elbow attaches the fifth end of the third arm to the first end of the first arm to form a right angle;
wherein the third end of the second arm inserts into the second end of the first arm to form the first telescopic structure;
wherein the eleventh end of the sixth arm inserts into the tenth end of the fifth arm to form the third telescopic structure;

wherein the second 90-degree elbow attaches the ninth end of the fifth arm to the thirteenth end of the seventh arm to form a right angle;
wherein the fifteenth end of the eighth arm inserts into the fourteenth end of the seventh arm to form the fourth telescopic structure;
wherein the twenty-third end of the twelfth arm inserts into the twenty-second end of the eleventh arm to form the sixth telescopic structure;
wherein the third 90-degree elbow attaches the twenty-first end of the eleventh arm to the seventeenth end of the ninth arm to form a right angle;
wherein the nineteenth end of the tenth arm inserts into the eighteenth end of the ninth arm to form the fifth telescopic structure;
wherein the twenty-seventh end of the fourteenth arm inserts into the twenty-sixth end of the thirteenth arm to form the seventh telescopic structure;
wherein the fourth 90-degree elbow attaches the twenty-fifth end of the thirteenth arm to the twenty-ninth end of the fifteenth arm to form a right angle;
wherein the thirty-first end of the sixteenth arm inserts into the thirtieth end of the fifteenth arm to form the eighth telescopic structure.

14. The therapeutic accessory according to claim 13
wherein the first gripping structure attaches to the fourth end of the second arm;
wherein the second gripping structure attaches to the sixteenth end of the eighth arm;
wherein the third gripping structure attaches to the twentieth end of the tenth arm;
wherein the fourth gripping structure attaches to the thirty-second end of the sixteenth arm.

15. The therapeutic accessory according to claim 14
wherein the span of the lengths of each of the first telescopic structure, the second telescopic structure, the third telescopic structure, the fourth telescopic structure, the fifth telescopic structure, the sixth telescopic structure, the seventh telescopic structure, and the eighth telescopic structure are set to form a framing area in the shape of a rectangular block;
wherein the framing area is sized such that the plurality of mounting brackets receives the feeding machine within the backpack.

16. The therapeutic accessory according to claim 15
wherein the first gripping structure is coated with an elastomeric material;
wherein the second gripping structure is coated with an elastomeric material;
wherein the third gripping structure is coated with an elastomeric material;
wherein the fourth gripping structure is coated with an elastomeric material.

* * * * *